United States Patent [19]

Takagaki

[11] Patent Number: 5,226,819
[45] Date of Patent: Jul. 13, 1993

[54] INTELLIGENCE TESTING DEVICE
[75] Inventor: Shuichi Takagaki, Fujiidera, Japan
[73] Assignee: Kyoto Densoku Kabushiki Kaisha, Kyoto, Japan
[21] Appl. No.: 849,030
[22] PCT Filed: Aug. 31, 1991
[86] PCT No.: PCT/JP91/01165
   § 371 Date: Apr. 22, 1992
   § 102(e) Date: Apr. 22, 1992
[87] PCT Pub. No.: WO92/03968
   PCT Pub. Date: Mar. 19, 1992

[30] Foreign Application Priority Data
   Sep. 3, 1990 [JP] Japan .................. 2-234160
[51] Int. Cl.$^5$ ................................ A61B 5/00
[52] U.S. Cl. ................................... 434/236
[58] Field of Search ............... 434/236–238, 434/222, 327, 331, 335, 338, 339, 353–359, 362; 178/18–20

[56] References Cited
U.S. PATENT DOCUMENTS
4,471,162 9/1984 Aono et al. ............... 178/19

OTHER PUBLICATIONS

Annual Bulletin of Kosei–Nenkin Hospitals vol. 14, 1987 "Analysis of Points–Preliminary Study" (pp. 283–290) Hayashi, et al.
Annual Bulletin of Kosei–Nenkin Hospitals vol. 156, 1988 "Analysis of Point–Preliminary Study (2)" (pp. 317–323) Hayashi, et al.
Annual Bulletin of Kosei–Nenkin Hospitals vol. 16, 1989 "Analysis of Pointing–Preliminary Study III" (pp. 323–337) Tanaka, et al.
Japanese Laid–Open Patent Publication No. 119,818 of 1989–Aoki, et al.
Japanese Utility Model Publication No. 10,777 of 1952–Ogimura, et al.

Primary Examiner—Richard J. Apley
Assistant Examiner—Glenn E. Richman
Attorney, Agent, or Firm—Morgan & Finnegan

[57] ABSTRACT

An intelligence testing device comprising a two dimensional coordinate reading device for reading coordinates of a distribution of dots which a testee has written upon receiving instructions to write dots randomly and dispersedly in a predetermined frame.

5 Claims, 11 Drawing Sheets

TIME (1/10 sec)

AVERAGE TIME $\overline{X}$ = 1.1 SECOND
DISPERSION R = 1.7 SECOND

FIG. 14B

| ID: 100001 | AGE: 32 |
|---|---|
| SEX: MALE | CONDITION: NORMAL |
| AVERAGE TIME: 1.1 ||
| 1 → 2.5 | 16 → 1.0 |
| 2 → 1.0 | 17 → 0.8 |
| 3 → 1.0 | 18 → 0.9 |
| 4 → 1.0 | 19 → 1.0 |
| 5 → 1.2 | 20 → 0.9 |
| 6 → 1.4 | 21 → 1.0 |
| 7 → 0.9 | 22 → 0.9 |
| 8 → 0.9 | 23 → 1.2 |
| 9 → 1.0 | 24 → 0.9 |
| 10 → 1.0 | 25 → 1.2 |
| 11 → 1.0 | 26 → 1.6 |
| 12 → 1.1 | 27 → 0.9 |
| 13 → 0.9 | 28 → 0.9 |
| 14 → 0.9 | 29 → 1.3 |
| 15 → 1.0 | 30 → 0.9 |

FIG. 15A

TIME (1/10 sec)

AVERAGE TIME $\bar{X}$ = 4.0 SECOND
DISPERSION R = 31.5 SECOND

FIG. 15B

| ID: 67373 | AGE: 68 |
|---|---|
| SEX: MALE | CONDITION: PATIENT |
| AVERAGE TIME: 4.0 ||
| 1 → 32.7 | 16 → 2.1 |
| 2 → 3.0 | 17 → 2.8 |
| 3 → 2.3 | 18 → 2.7 |
| 4 → 2.5 | 19 → 1.8 |
| 5 → 1.2 | 20 → 1.6 |
| 6 → 2.1 | 21 → 2.5 |
| 7 → 12.2 | 22 → 1.9 |
| 8 → 2.1 | 23 → 4.1 |
| 9 → 2.7 | 24 → 1.7 |
| 10 → 2.0 | 25 → 1.7 |
| 11 → 8.2 | 26 → 2.2 |
| 12 → 2.6 | 27 → 2.9 |
| 13 → 2.4 | 28 → 3.3 |
| 14 → 2.6 | 29 → 2.8 |
| 15 → 1.5 | 30 → 2.5 |

| ID: 100001 | AGE: 32 |
|---|---|
| SEX: MALE | CONDITION: NORMAL |
| AVERAGE SPEED: 6.7 | |
| 1 → 2 : 3.0 | 16 → 17 : 5.2 |
| 2 → 3 : 3.6 | 17 → 18 : 11.8 |
| 3 → 4 : 6.0 | 18 → 19 : 4.0 |
| 4 → 5 : 4.5 | 19 → 20 : 5.6 |
| 5 → 6 : 2.3 | 20 → 21 : 7.2 |
| 6 → 7 : 8.9 | 21 → 22 : 4.0 |
| 7 → 8 : 10.1 | 22 → 23 : 5.3 |
| 8 → 9 : 7.6 | 23 → 24 : 5.6 |
| 9 → 10 : 5.4 | 24 → 25 : 4.2 |
| 10 → 11 : 12.6 | 25 → 26 : 6.2 |
| 11 → 12 : 11.1 | 26 → 27 : 6.5 |
| 12 → 13 : 6.8 | 27 → 28 : 4.0 |
| 13 → 14 : 11.4 | 28 → 29 : 10.0 |
| 14 → 15 : 9.0 | 29 → 30 : 7.0 |
| 15 → 16 : 6.4 | |

| ID: 67373 | AGE: 68 |
|---|---|
| SEX: MALE | CONDITION: PATIENT |
| AVERAGE SPEED: 1.1 | |
| 1 → 2 : 0.5 | 16 → 17 : 1.9 |
| 2 → 3 : 0.6 | 17 → 18 : 2.5 |
| 3 → 4 : 0.6 | 18 → 19 : 0.8 |
| 4 → 5 : 1.2 | 19 → 20 : 1.2 |
| 5 → 6 : 1.3 | 20 → 21 : 0.9 |
| 6 → 7 : 0.2 | 21 → 22 : 1.2 |
| 7 → 8 : 1.3 | 22 → 23 : 0.3 |
| 8 → 9 : 0.5 | 23 → 24 : 3.7 |
| 9 → 10 : 0.7 | 24 → 25 : 1.2 |
| 10 → 11 : 0.2 | 25 → 26 : 2.3 |
| 11 → 12 : 0.5 | 26 → 27 : 1.2 |
| 12 → 13 : 1.8 | 27 → 28 : 1.8 |
| 13 → 14 : 0.5 | 28 → 29 : 0.8 |
| 14 → 15 : 0.9 | 29 → 30 : 1.2 |
| 15 → 16 : 0.7 | |

INTELLIGENCE TESTING DEVICE

TECHNICAL FIELD

This invention relates to an intelligence testing device.

BACKGROUND ART

Recently, in the department of neuropsychiatry, an intelligence testing method has been proposed for knowing the degree of advancement of intelligence or diagnosing aging and dementia.

As for conventional techniques, tests for finding a decrease in the mentation of old people include a Hasegawa type dementia scale and an N-type mentation test. These tests judge whether or not a subject can correctly answer questions concerning orientation and impressibility.

On the other hand, according to what is experienced in picture drawing therapy, pictures drawn by many old people are characterized by loss of freedom and collapse of form. This suggests that a decrease in mentation can be surmised from pictures. However, pictures themselves contain so much information that quantitization is difficult. Therefore, development of a method of judgement was started in about 1987, which method, substituting the act of "marking points" which is the simplest form of drawing pictures, is based on the analysis of distribution or locus of points (references: "ANALYSIS OF POINTS"—PRELIMINARY STUDY, Mikio Hayashi and Toshikazu Hakamada, Kosei-Nenkin Hospital Annual Report Vol. 14 (1987), pp. 283-290; "ANALYSIS OF POINTS"—PRELIMINARY STUDY II, Mikio Hayashi, Makiko Tominaga and Syuniti Hakamada, Kosei-Nenkin Hospital Annual Report Vol. 15 (1988), pp. 317-323; "EARLY DETECTION OF DEMENTIA IN PICTURE THERAPY", Mikio Hayasi and Chitaru Tanaka, in CLINICAL PICTURE STUDY IV (1988), published by Kongo Publishing Co., Ltd., pp. 33-48, "ANALYSIS OF POINTS"—PRELIMINARY STUDY III, Mikio Hayashi and Chitaru Tanaka, Kosei Nenkin Hospital Annual Report Vol. 16 (1989), pp. 323-339). The principle of this "point analysing method" consists of instructing a subject to enter a plurality of points (I points) randomly and distributively in M (vertical)×N (horizontal) quadratures and specifying the positions of the points by the coordinates of the quadratures in which they are entered.

As a precondition, let the horizontal direction of the quadratures be called the x direction and the vertical direction thereof the y direction. As the numbers adopted since the beginning of the development of the method, the number of columns (the number of quadratures in the x direction) M=12 and the number of rows (the number of quadratures in the y direction) N=20 and the number of entered points I=30. If the i-th entered point (i=1, 2, ..., 3) is entered in a quadrature which is located at the $a_i$-th position from the left and $b_i$-th position from the top, the coordinates of said point are $(a_i, b_i)$. In this case, $a_i$ and $b_i$ are integers which satisfy the relations $1 \leq a_i \leq 12$ and $1 \leq b_i \leq 20$.

Let $\{(u_i, v_i)\}$ be the progression of difference in the order sequence $\{(a_i, b_i)\}$ of the coordinates of the 30 points. That is, $$u_i = a_{i+1} - a_i$$

$$v_i = b_{i+1} - b_i$$

In this case, i=1, 2, ..., 29.

As is clear from this definition, $u_i$ and $v_i$ are integers which satisfy the relations:

$$-11 \leq u_i \leq 11,$$

$$-19 \leq v_i \leq 19.$$

(1) First method: dispersion in distribution of points

Let $m_k$ be the number of points i whose x coordinates satisfy the relation $a_i = k$, that is, which belong to the k-th column, and let $n_t$ be the number of points i whose y coordinates satisfy the relation $b_i = t$, that is, which belong to the t-th column.

Then $D_x$ and $D_y$ are found as follows.

$$D_x = \sum_{K=1}^{M} |m_K - I/M|$$

$$D_x = \sum_{K=1}^{12} |m_K - 5/2|$$

$$D_y = \sum_{t=1}^{N} |n_t - I/N|$$

$$D_y = \sum_{t=1}^{20} |n_t - 3/2|$$

Since I/M=5/2 and I/N=3/2 are the total number of marked points divided by the number of columns and by the number of rows, respectively, they are values which should be the average number of marked points in each column and each row in a large number of samples in which the points are marked truly at random. Therefore, $D_x$ and $D_y$ respectively represent the sums of deviations from the average values of the numbers of actually marked points in each column and each row. The coordinates $(D_x, D_y)$ are specified and the lowering in mentation is judged from the positional relation to the origin or normal range (to be later described).

(2) Second method: Amount of movement of dispersion

Each of the progression of difference $\{(u_i, v_i)\}$ represents the distances (the numbers of quadratures) in the row and column directions traveled from the i-th marked point to the i+1-th marked point, the sum of $|u_i|$ (i=1, 2, ..., 29) and the sum of $|v_i|$ (i=1, 2, ..., 29) represent the sizes of dispersions of marked points in each direction.

That is, $$X = \sum_{i=1}^{I-1} |u_i| \quad (\text{where } I - 1 = 29)$$

$$Y = \sum_{i=1}^{I-1} |v_i| \quad (\text{where } I - 1 = 29)$$

and, $$S = XY$$

where S is called the amount of movement. In this example, S is compared with a preset reference value $S_o = 7900$ and if S is found greater than said reference value, the mentation is judged to be normal and if it is smaller than said reference value the mentation is judged to have been lowered.

(3) Third method: dispersion of movement (displacement)

Let $v_k$ be the number of points i which satisfy the displacement of marked points in the x direction, $u_i = k$, that is, the number of occurrences of the displacement k in the x direction, and let $\lambda_t$ be the number of points i which satisfy the displacement of marked points in the y direction, $v_i = t$, that is, the number of occurrences of the displacement t in the y direction.

Then, $T_x$ and $T_y$ are found as follows:

$$T_x = \sum_{k=-(M-1)}^{M-1} \left| v_k - - \frac{M - |k|}{M^2} \times (I - 1) \right|$$

$$= \sum_{k=-11}^{11} \left| v_k - - \frac{12 - |k|}{144} \times 29 \right|$$

$$T_y = \sum_{t=-(N-1)}^{N-1} \left| \lambda_t - - \frac{N - |t|}{N^2} \times (I - 1) \right|$$

$$= \sum_{t=-19}^{19} \left| \lambda_t - - \frac{20 - |t|}{400} \times 29 \right|$$

The coordinates ($T_x$, $T_y$) specify points presented by the sample.

The meaning of $T_x$, $T_y$ is as follows. The values which the representative value $a_i$ in the sequence $\{a_i\}$ can take are integers ranging from 1 to M=12. Then, $u_i$ can be values $-(M-1)$, $-(M-2)-\ldots-1, 0, 1, \ldots, M-1$. Therefore, when $k \geq 0$, there are $M \times k$ ways in which $u_i = k$, as shown in Table I.

TABLE 1

| $a_i$ | 1 | 2 | ... | M − k |
|---|---|---|---|---|
| $a_{i+1}$ | k + 1 | k + 2 | ... | M |

Similarly, when $k < 0$, there are $M - |k|$ ways.

If each term in $\{a_i\}$ is independent, then the occurrences of all sets of $a_i$ and $a_{i+1}$ which have $M \times M$ ways are of equal probability. It is seen from the above discussion that since there are $M - |k|$ ways in which $u_i = k$, the probability of $u_i = k$ is $f(x) = (M - |k|)/M^2$ (the second term in the $T_x$ equation)

Since $\{a_i\}$ consists of $I - 1 = 29$ terms, the average value of the frequency of occurrence of i such that $u_i = k$ is $29 \times f(x)$ if the marking of points is at random. (This applies also to the sequence $\{b_i\}$, and the $T_y$ equation holds.)

After all, it will be understood that $T_x$ and $T_y$ are quantities indicating how much the frequency of occurrence of displacement in the x and y directions deviates from the frequency of occurrence which obeys this probability distribution. However, it should be noted that in a strict sense, the independence of $a_i$ and $a_{i+1}$ does not hold. The reason is that two points cannot occupy the same quadrature at the same time. However, since $T_x$ and $T_y$ are considered to be a single function which substantially formularizes the dispersion of displacement (movement), it is not necessary to treat $f(K)$ as probability distribution in a strict sense. In brief, it s important that $T_x$ and $T_y$ form a function such that there is a difference between a group of patients and a control group (a group of subjects to be considered normal).

(4) Dispersion index ($D_x$, $D_y$) and ($T_x$, $T_y$) represent "dispersion of distribution of points" and "dispersion of movement of points" of a sample, respectively. The linear combination of these quantities is referred to as "dispersion index". That is, the "dispersion index of coefficient $\mu$": ($V_x$, $V_y$)$_\mu$ is defined by the following formula.

$$(V_x, V_y)_\mu = (D_x, D_y) + \mu(T_x, T_y)$$

where $\mu > 0$.

To evaluate the test results, the calculated values for the respective subjects are plotted on a graph. Similar tests are conducted in advance on healthy person to find the range of healthy person, it being surmised that the further the calculated values are deviated from this range drawn on the same graph, the greater the degree of dementia. In this case, the normal ranges of the calculated values ($D_x$, $D_y$) according to the first method and the calculated values ($T_x$, $T_y$) according to the third method are circles having center coordinates substantially determined by probability calculations, while in the second method judged by the product S of the x-coordinate X and y-coordinate, the normal range is a hyperbola (only in the first quadrant) expressed by $xy = S_o$ (where $S_o$ is a constant, which is 7900 in the above example), and it is judged that the upper right of the hyperbola is normal and the lower left means that there is a decrease in mentation.

In conventional tests, a subject is instructed to mark points on a test paper sheet. Although the coordinates of points can be found from the collected paper sheet, the order in which the points are entered cannot be found; therefore, the numbers of points in the columns and rows are visually counted, and from the counted results, calculations according to the first method are made by writing or by using a computer. In addition, the second and third methods requiring information on the order of marking the points have been experimentally verified by telling a subject to enter numerals rather than points.

DISCLOSURE OF THE INVENTION

However, if the result of analysis is to be found by calculations using such method, the time taken in calculations would be so long that a quick judgement cannot be expected. Further, it is also possible to know the degree of advancement of dementia from other pieces of information included in the test result, such as the distance to the next point, direction, movement and the time taken to mark each point; however, such analysis cannot be made by using the conventional method described above.

In judging the degree of advancement of dementia by telling a subject to mark a plurality of points on a test paper sheet, this invention is intended to accelerate the test thereof and make it possible to reproduce the test.

This invention provides an intelligence testing device, which uses a two-dimensional coordinate reader to automatically read the coordinates of each quadrant of a test paper sheet having a point marked therein, said coordinates being stored in a storage device together with the order of marking the points and the time interval or lapse of time between successive points, these pieces of stored information being fed to a central processing unit and arithmetically processed according to a preset program, said intelligence testing device including a display device for graphically displaying the result of the arithmetic operation.

According to the above arrangement, the quadratures in each column of a test paper sheet are read by the two-dimensional coordinate reader. The information on the coordinates thus read is fed to the central processing unit (CPU), where the necessary arithmetic operation is performed. The result of the arithmetic operation, i.e., the test result is immediately obtained and displayed on a graph. Further, by the storage device which stores the positions of marked points, their order and periods of time, the situation in which the test proceeds can be easily reproduced at any time required.

BEST MODE FOR EMBODYING THE INVENTION

Figure 1:
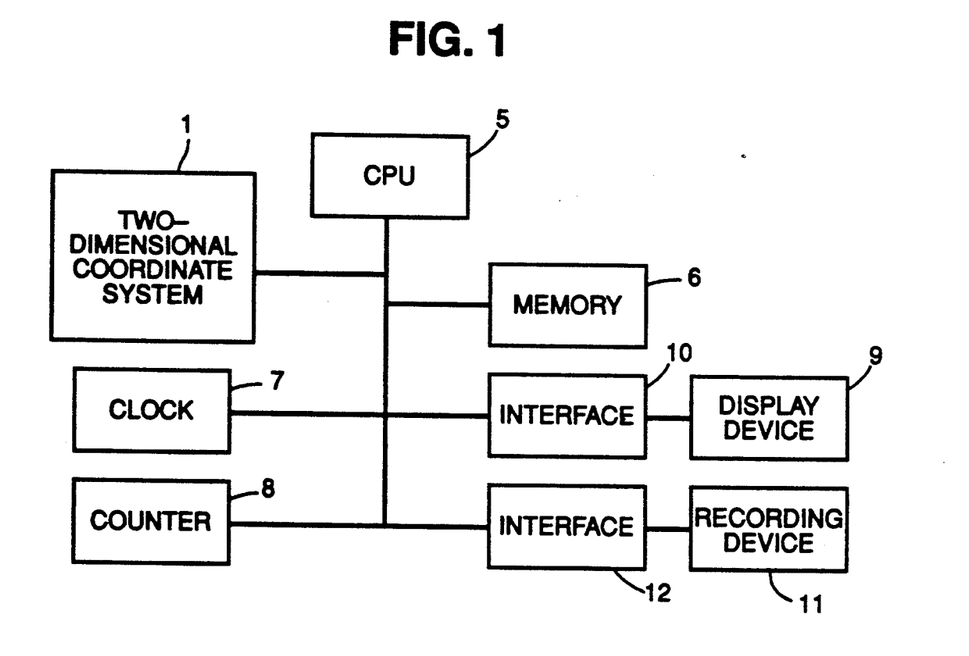
FIG. 1 is a block diagram showing an intelligence testing device according to an embodiment of the present invention.

An embodiment of this invention will now be described with reference to FIGS. 1 and 2. The numeral 1 denotes a two-dimensional coordinate reader known as a digitizer, adapted to support a test paper sheet so that when a point is marked in a quadrature of the test paper sheet, it automatically reads the coordinates of the point.

Figure 2:
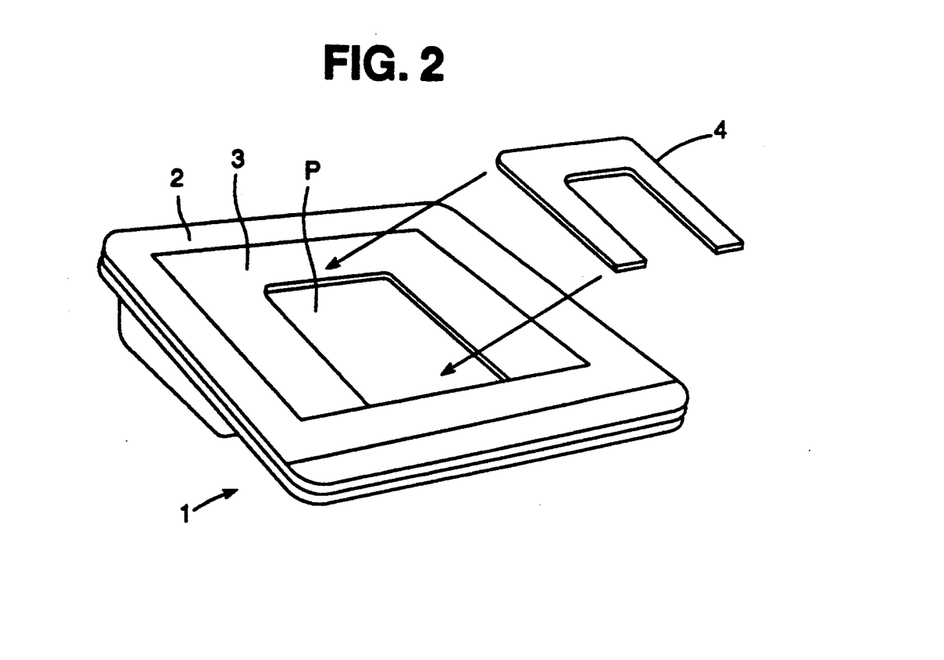
FIG. 2 is a perspective view showing an example of the construction of the two-dimensional coordinate reader device included in the device of FIG. 1.

FIG. 2 shows an example of the construction thereof. The two-dimensional coordinate reader 1 is provided with a reading base block 2 for supporting a test paper sheet P thereon. The numeral 3 denotes a frame plate for controlling the position of the test paper sheet P and 4 denotes a plate for holding the peripheral edge of the test paper sheet P placed thereon. This two-dimensional coordinate reader is based on the principle of, for example, in the system disclosed in Japanese Patent Application Disclosure No. 119818/1989, periodically generating an upwardly directed electromagnetic field alternately in either of the X/Y directions while scanning, detecting said electromagnetic field by a coordinate indicator containing a tuning circuit integral with a writing utensil, detecting an electromagnetic field produced in the digitizer on the basis of the tuning thereof by the coordinate indicator while scanning in the other of the X, Y directions on the side associated with the digitizer, thereby taking out the coordinate value of the tuning point from the intersection of the transmission and reception XY scannings.

The numeral 5 denotes a CPU for taking out from the memory 6 the information read by the two-dimensional coordinate reader 1, that is, the coordinates of the quadratures in which points are marked and the order of marking the points, and then performs the necessary calculations, for example, in the case of the first method, the absolute value of the difference between the statistic average number of rows or columns of the test paper sheet, and the number of points, and the sum thereof. These calculations may, of course, comprise other arithmetic procedures, for example, substituting the distance between points and the direction, time and speed of the marking of points.

The memory 6 stores the coordinates of a marked point and the time taken in marking the point, said time being measured by a clock device 7. The numeral 8 denotes a counter for counting the number of marked points. In this example, when 80 points are marked, this fact is reported. Upon completion of the marking of 30 points, arithmetic operations are performed by the CPU 5.

In addition, in the case where the same quadrature is marked twice or more with a point or where other places than the quadratures are marked with points, such points are not counted, with their coordinates annulled.

The numeral 9 denotes a display device for receiving the result of calculations from the CPU 5 through an interface 10, whereby the result of calculations is graphically displayed. As said display device, use is made of a printer, CRT or the like.

The numeral 11 denotes a recording device for receiving the result of calculations from the CPU 5 through an interface 12, whereby the result of calculations is recorded. As said recording device, use is made of a floppy disk or the like.

Figure 3:
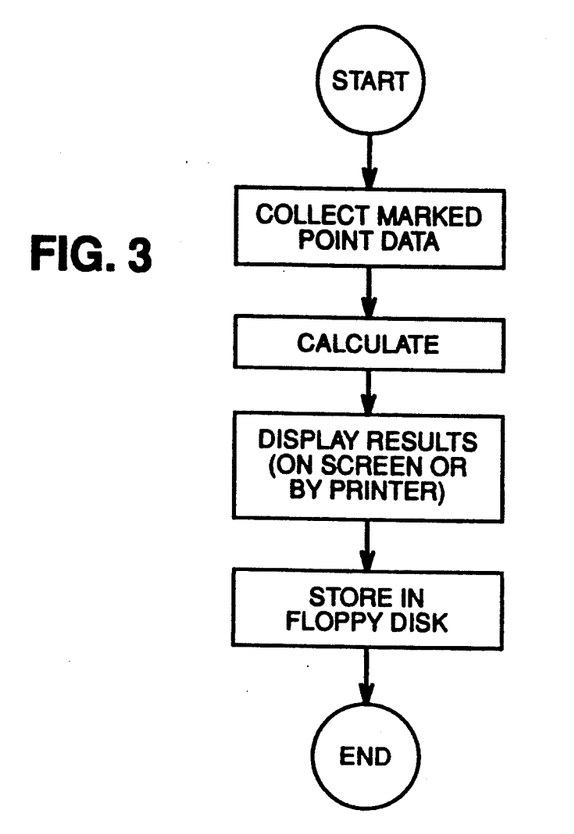
FIG. 3 is a flowchart showing the procedures for performing intelligence test and analysis using the device arrangement of the present invention.
Figure 4:
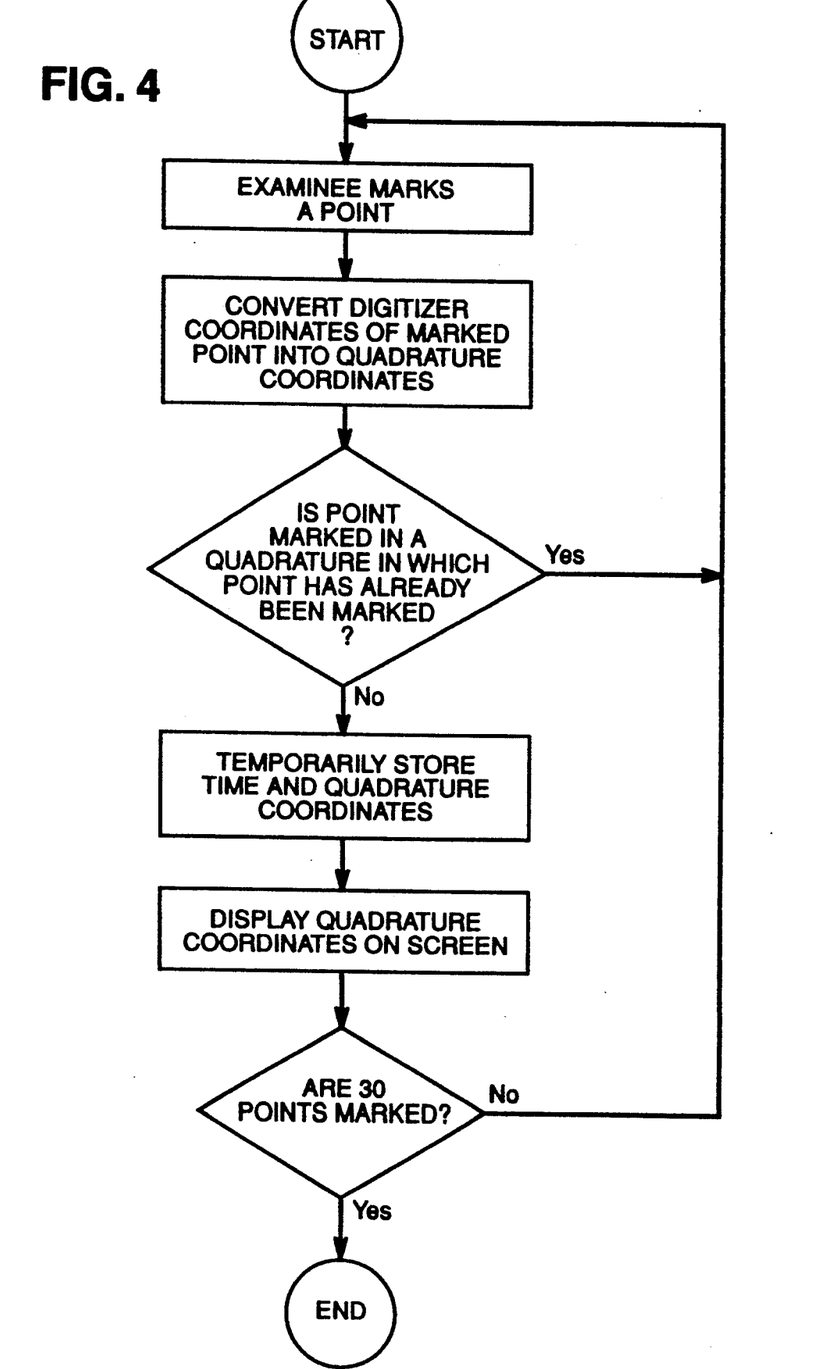
FIG. 4 is a flowchart showing the contents of point data collecting procedure which is the first step in the flowchart shown in FIG. 3.
Figure 5:
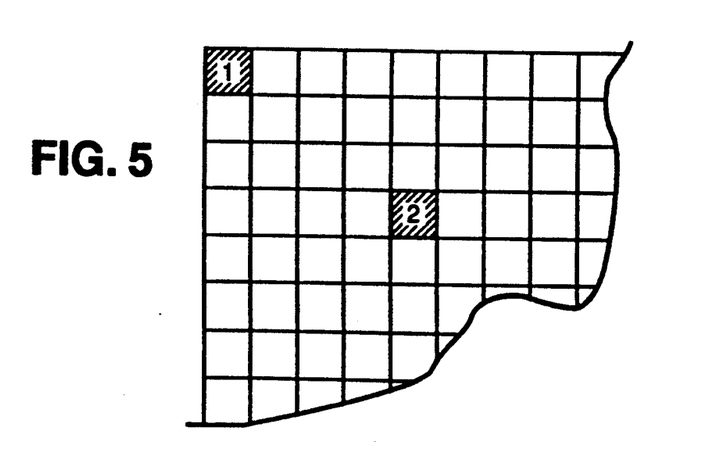
FIG. 5 is a marked point diagram displayed on a display device as marked point data collecting procedure proceeds.

FIG. 3 is a flowchart showing the procedure for performing intelligence tests and analysis by using the device arrangement of the present invention described above. FIG. 4 is a flowchart showing the contents of the point marking data collecting procedure which is the first stage of the system flow shown in FIG. 3. FIG. 5 is a point marking diagram displayed on a display device as marked point data collecting procedure proceeds. The screen of the display device (an exclusive section for displaying marked points may be provided) has quadratures drawn thereon in advance, and it is arranged that the colors of quadratures in which points are marked change and that numerals indicating the order of marking the points appear in the quadratures.

VERIFICATION EXAMPLE

Figure 6:
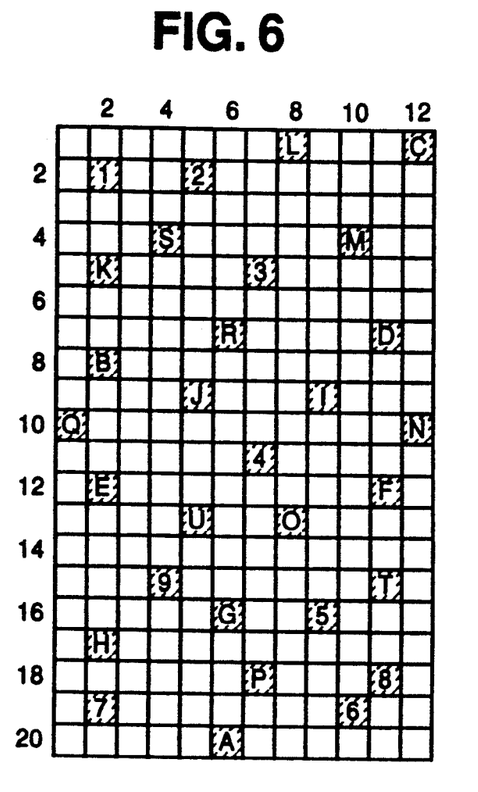
FIG. 6 shows the distribution of points marked by a normal person, displayed on a display screen.
Figure 7:
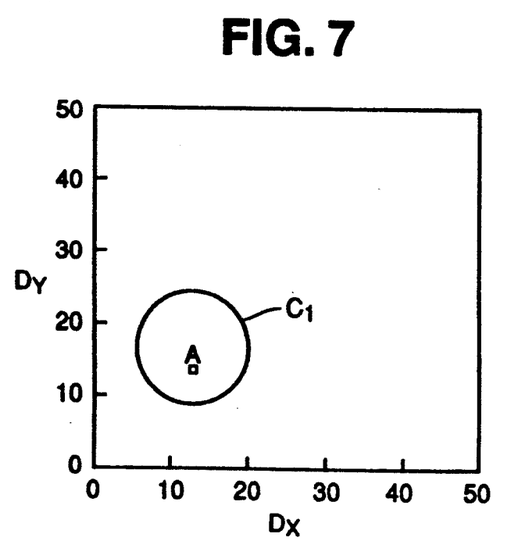
FIGS. 7 through 9 are graphs showing the results obtained by arithmetically processing said marked point ditribution by the first, second and third methods, respectively.
Figure 8:
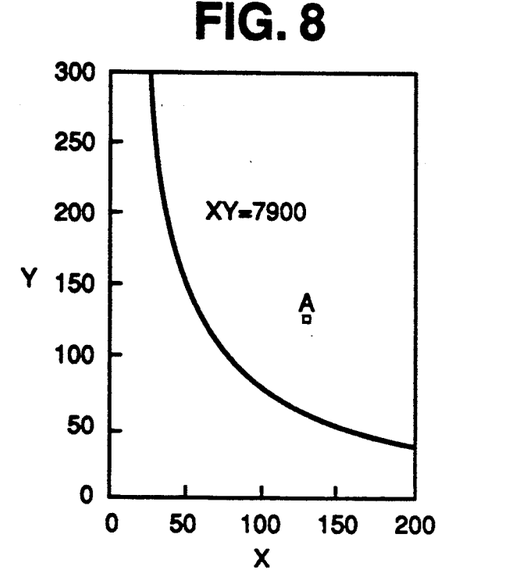
Figure 9:
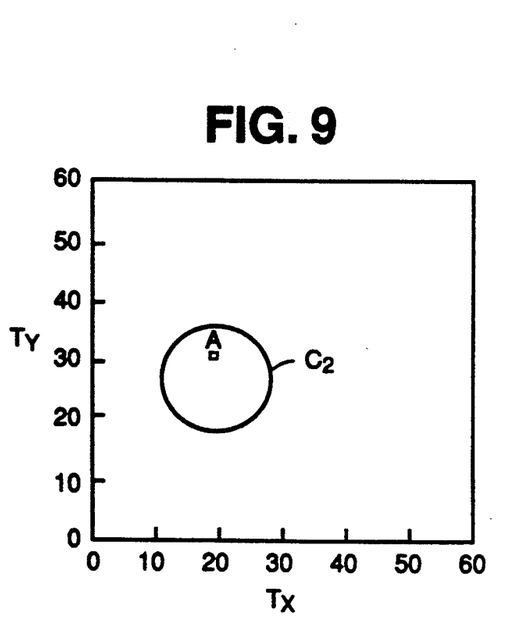
Figure 10:
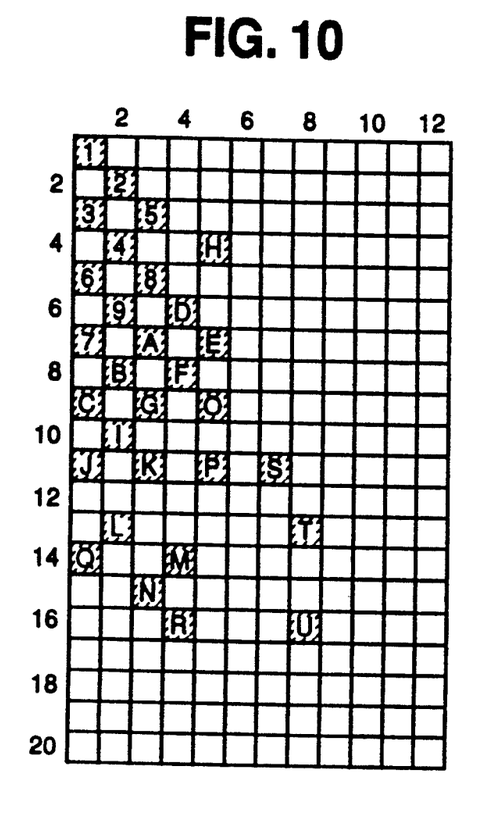
FIG. 10 shows the distribution of points marked by a patient, displayed on the display screen of the device.
Figure 11:
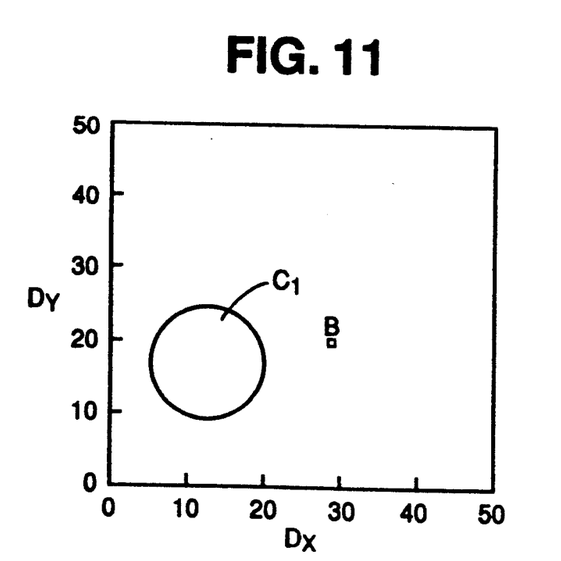
FIGS. 11 through 13 are graphs showing the results obtained by arithmetically processing the patient's marked point distribution by the first, second and third methods.
Figure 12:
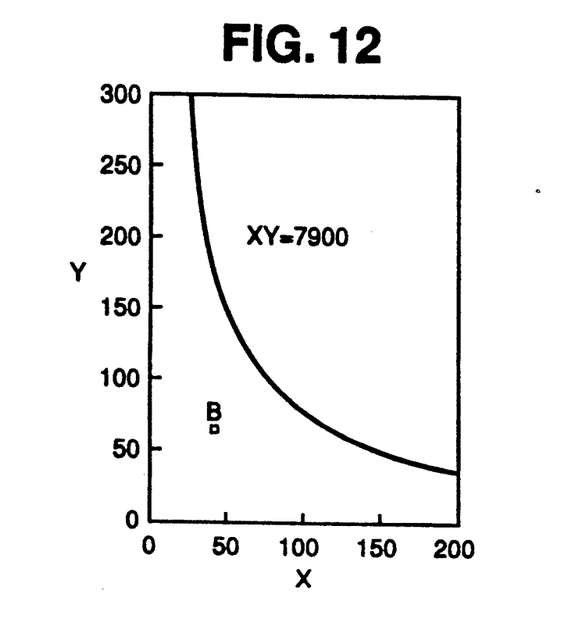
Figure 13:
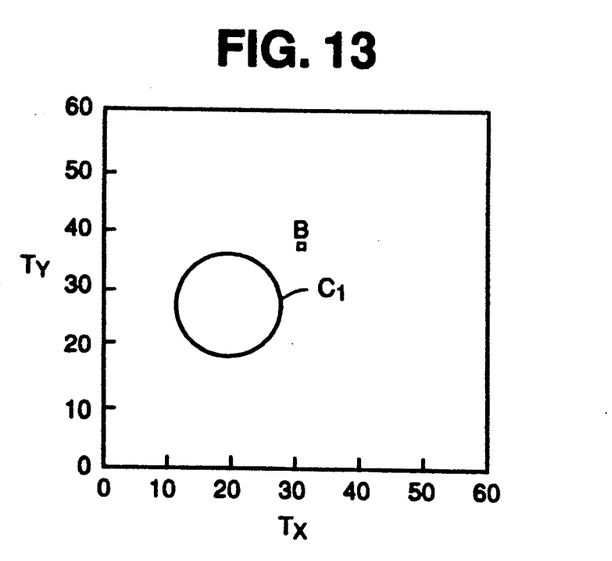

FIG. 6 shows the distribution of points marked by a normal person, displayed on a display screen; FIGS. 7 through 9 are graphs showing the results obtained by arithmetically processing said marked point ditribution by the first, second and third methods, respectively; FIG. 10 shows the distribution of points marked by a patient, displayed on the display screen of the device; FIGS. 11 through 13 are graphs showing the results obtained by arithmetically processing the patient's marked point distribution by the first, second and third methods. In addition, in FIGS. 6 and 10, the order of marking the points (hatched quadratures) is indicated by the corresponding numerals for the first through ninth points and the English letters A through U for the 10th through 30th points.

Concerning an examinee A (normal person, 32-year old male), the calculating method and graphic representation will now be described.

FIRST METHOD

| Column number (k) | 1 | 2 | 3 | 4 | 5 | 6 | 7 | 8 | 9 | 10 | 11 | 12 |
|---|---|---|---|---|---|---|---|---|---|---|---|---|
| Number of quadratures ($m_k$) | 1 | 6 | 0 | 2 | 3 | 3 | 3 | 2 | 2 | 2 | 4 | 2 |
| Dispersion in distribution $\|m_k - 2.5\|$ | 1.5 | 3.5 | 2.5 | 0.5 | 0.5 | 0.5 | 0.5 | 0.5 | 0.5 | 0.5 | 1.5 | 0.5 |

(1) The number of quadratures marked with points and dispersion in distribution in each column

| Row number (t) | 1 | 2 | 3 | 4 | 5 | 6 | 7 | 8 | 9 | 10 |
|---|---|---|---|---|---|---|---|---|---|---|
| Number of quadratures ($n_t$) | 2 | 2 | 0 | 2 | 2 | 0 | 2 | 1 | 2 | 2 |
| Dispersion in distribution $\|n_t - 1.5\|$ | 0.5 | 0.5 | 1.5 | 0.5 | 0.5 | 1.5 | 0.5 | 0.5 | 0.5 | 0.5 |

(2) The number of quadratures marked with points and dispersion in distribution in each row

| Row number (t) | 11 | 12 | 13 | 14 | 15 | 16 | 17 | 18 | 19 | 20 |
|---|---|---|---|---|---|---|---|---|---|---|
| Number of quadratures ($n_t$) | 1 | 2 | 2 | 0 | 2 | 2 | 1 | 2 | 2 | 1 |
| Dispersion in distribution $\|n_t - 1.5\|$ | 0.5 | 0.5 | 1.5 | 1.5 | 0.5 | 0.5 | 0.5 | 0.5 | 0.5 | 0.5 |

(3) Graphical representation of $D_x$ and $D_y$
$D_x = 1.5 \times 2 + 3.5 + 2.5 + 0.5 \times 8$
$= 13$
$D_y = 0.5 \times 1.7 + 1.5 \times 3$
$= 8.5 + 4.5$
$= 13$ Therefore, referring to FIG. 7, the coordinates ($D_x$, $D_y$) of the examinee A are satisfactorily located in a normal circle C1 (center coordinates: 12.9, 16.2).

SECOND METHOD (1) Progression of differences in displacement of marked points
x-direction $\{u_i\}_{i=1-29}$
3, 2, 0, 2, 1, 8$^-$, 9, 7$^-$, 2, 4$^-$, 10, 1$^-$,
9$^-$, 9, 5$^-$, 4$^-$, 7, 4$^-$, 3$^-$, 6, 2, 2, 4$^-$, 1$^-$, $$X = \sum_{i=1}^{29} |u_i| = 131$$

y-direction $\{v_i\}_{i=1-29}$
0, 4$^-$, 6$^-$, 5$^-$, 3$^-$, 0, 1, 3, 5$^-$, 12, 7, 6$^-$,
5$^-$, 0, 4$^-$, 1, 8, 9, 4, 4$^-$, 3$^-$, 6$^-$, 3$^-$, 5$^-$,
8, 3, 3, 11$^-$, 2

$$Y = \sum_{i=1}^{29} |v_i| = 122$$

$$\therefore S = XY = 15982$$

Thus, Since S=15982 is sufficiently greater than 7900, it is seen from FIG. 8 that the (x, y) coordinates of the examinee are within the upper right region (normal region) of the reference curve of XY=7900.

THIRD METHOD (1) $v_k$ and $\lambda_t$

Referring to the $u_i$ progression of the second method;

| $v_{-11}$ | $v_{-10}$ | $v_{-9}$ | $v_{-8}$ | $v_{-7}$ | $v_{-6}$ | $v_{-5}$ | $v_{-4}$ |
|---|---|---|---|---|---|---|---|
| 0 | 0 | 1 | 1 | 1 | 2 | 1 | 4 |

| $v_{-3}$ | $v_{-2}$ | $v_{-1}$ | $v_0$ | $v_1$ | $v_2$ | $v_3$ | $v_4$ |
|---|---|---|---|---|---|---|---|
| 1 | 1 | 2 | 0 | 1 | 5 | 1 | 0 |

| $v_5$ | $v_6$ | $v_7$ | $v_8$ | $v_9$ | $v_{10}$ | $v_{11}$ |
|---|---|---|---|---|---|---|
| 1 | 1 | 2 | 0 | 2 | 1 | 0 |

Similarly, referring to the $v_i$ progression of the second method;

| $\lambda_{-19}$ | $\lambda_{-18}$ | $\lambda_{-17}$ | $\lambda_{-16}$ | $\lambda_{-15}$ | $\lambda_{-14}$ | $\lambda_{-13}$ | $\lambda_{-12}$ |
|---|---|---|---|---|---|---|---|
| 0 | 0 | 0 | 0 | 0 | 0 | 0 | 0 |

| $\lambda_{-11}$ | $\lambda_{-10}$ | $\lambda_{-9}$ | $\lambda_{-8}$ | $\lambda_{-7}$ | $\lambda_{-6}$ | $\lambda_{-5}$ | $\lambda_{-4}$ |
|---|---|---|---|---|---|---|---|
| 1 | 0 | 0 | 0 | 0 | 6 | 4 | 2 |

| $\lambda_{-3}$ | $\lambda_{-2}$ | $\lambda_{-1}$ | $\lambda_0$ | $\lambda_1$ | $\lambda_2$ | $\lambda_3$ | $\lambda_4$ |
|---|---|---|---|---|---|---|---|
| 2 | 0 | 1 | 0 | 1 | 1 | 3 | 2 |

| $\lambda_5$ | $\lambda_6$ | $\lambda_7$ | $\lambda_8$ | $\lambda_9$ | $\lambda_{10}$ | $\lambda_{11}$ | $\lambda_{12}$ |
|---|---|---|---|---|---|---|---|
| 0 | 0 | 1 | 2 | 0 | 0 | 0 | 1 |

| $\lambda_{13}$ | $\lambda_{14}$ | $\lambda_{15}$ | $\lambda_{16}$ | $\lambda_{17}$ | $\lambda_{18}$ | $\lambda_{19}$ |
|---|---|---|---|---|---|---|
| 0 | 0 | 0 | 0 | 0 | 0 | 0 |

Using the above values, $$T_x = \sum_{k=-11}^{11} \left| v_k - \frac{12 - |k|}{144} 29 \right| = 19.9$$

$$T_y = \sum_{t=-19}^{19} \left| \lambda_t - \frac{20 - |t|}{400} 29 \right| = 29.9$$

Thus, referring to FIG. 9, the coordinates ($T_x$, $T_y$) of the examinee is located in the normal circle C2 (center coordinates: 19.6, 26.2) which is statistically determined.

The calculating method is similarly applied to an examinee B (patient, 68-year old male person). In the first method, Dx=29.0 and Dy=19.0, the coordinates are greatly deviated to the right from the normal circle C1 of FIG. 11, and in the second method, X=43 and Y=59 so that S=2537 and S<(XY=7900); thus in FIG. 12, the coordinates are located in the lower left region (mentation decrease region) of the reference curve. In the third method, $T_x$=30.7 and $T_y$=36.0 and it is seen from FIG. 13 that the coordinates are located outside the normal circle C2.

Figure 14A:
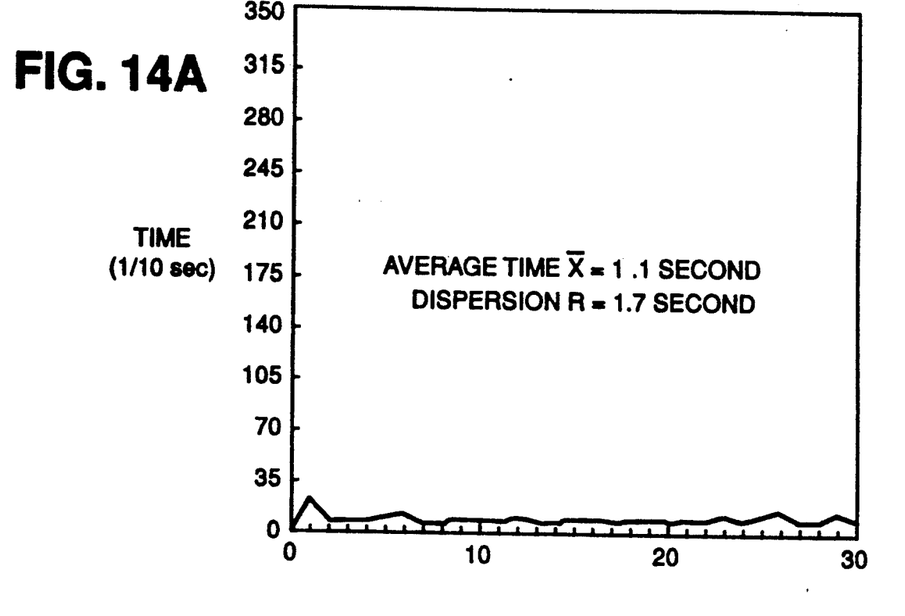
FIGS. 14 and 15 show the periods of time taken for said normal person and patient to mark points, displayed on a screen or a recording paper sheet.
Figure 14B:
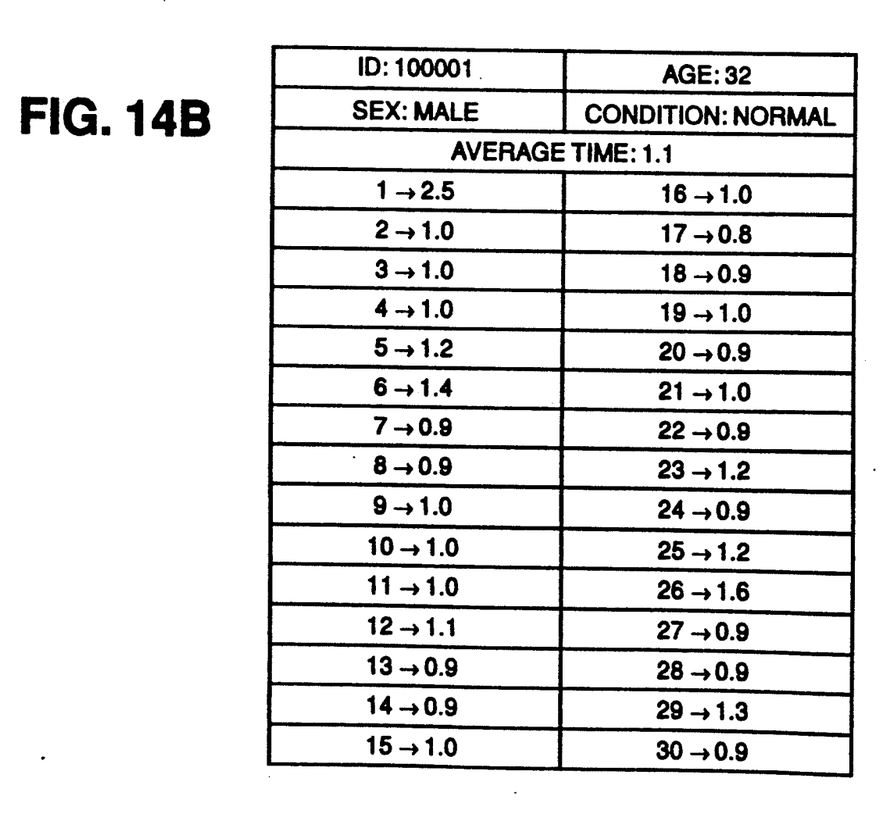
Figure 15A:
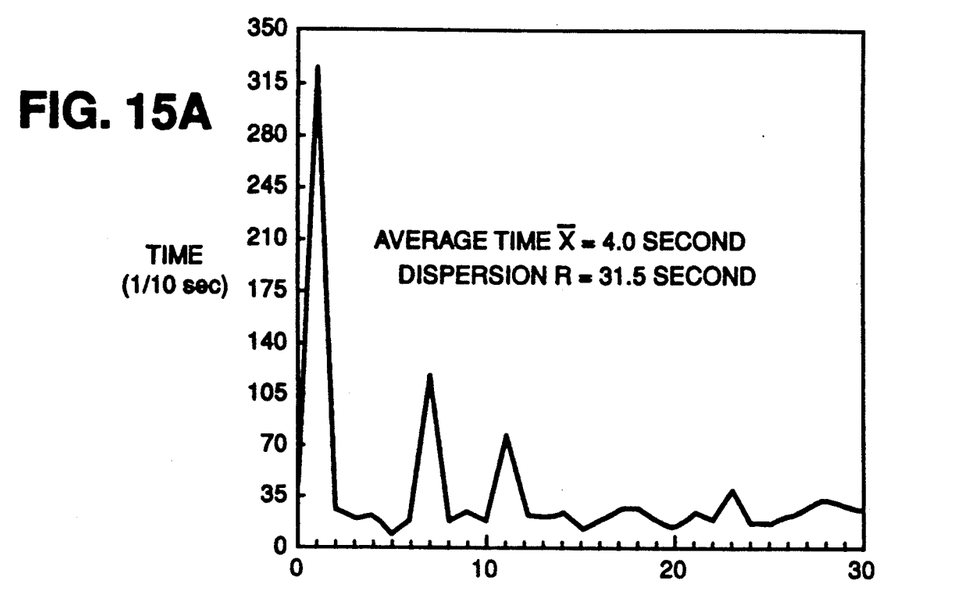
Figure 15B:
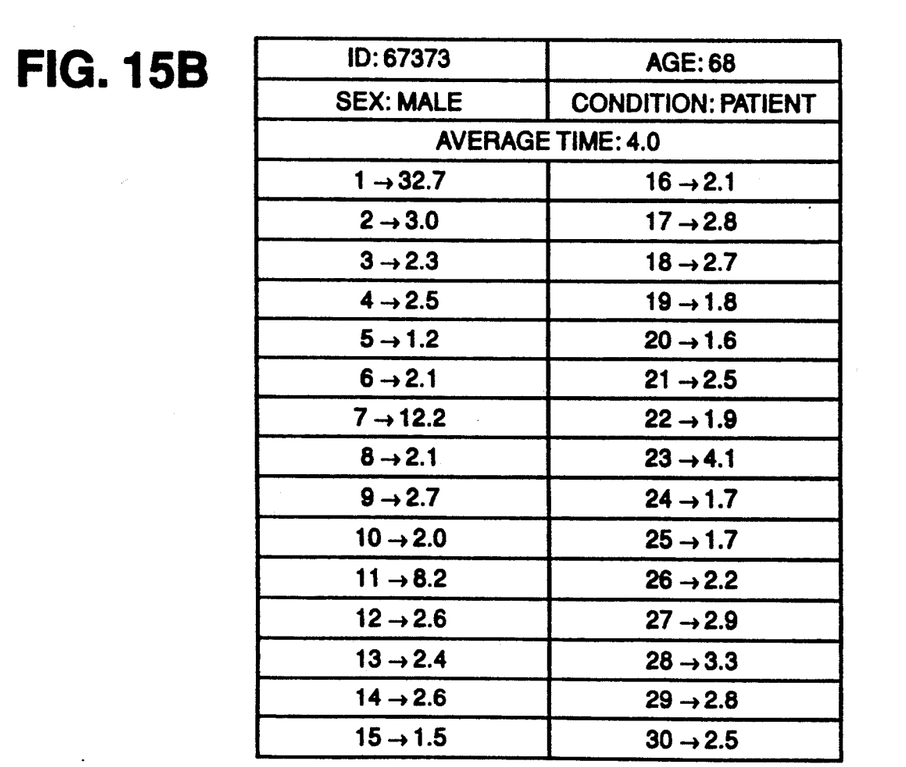

FIGS. 14 and 15 show the periods of time taken for the examinees A and B to mark points, displayed on a screen or a recording paper sheet. In the graph (a) in each figure, time is plotted on the vertical axis (unit:

1/10 second) and the number of each point is plotted on the horizontal axis. Thus, for example, the numeral 10 on the horizontal axis indicates the transfer of a marked point from the 9th to the 10th. The tables (b) indicate the time between successive points (unit: second).

A comparison between FIGS. 14 and 15 reveals that the patient B has a greater value for the average time ($\overline{X}$) than the normal person A and a greater value for the difference (dispersion R) between the maximum value and the minimum of the time between successive points.

Figure 16A:
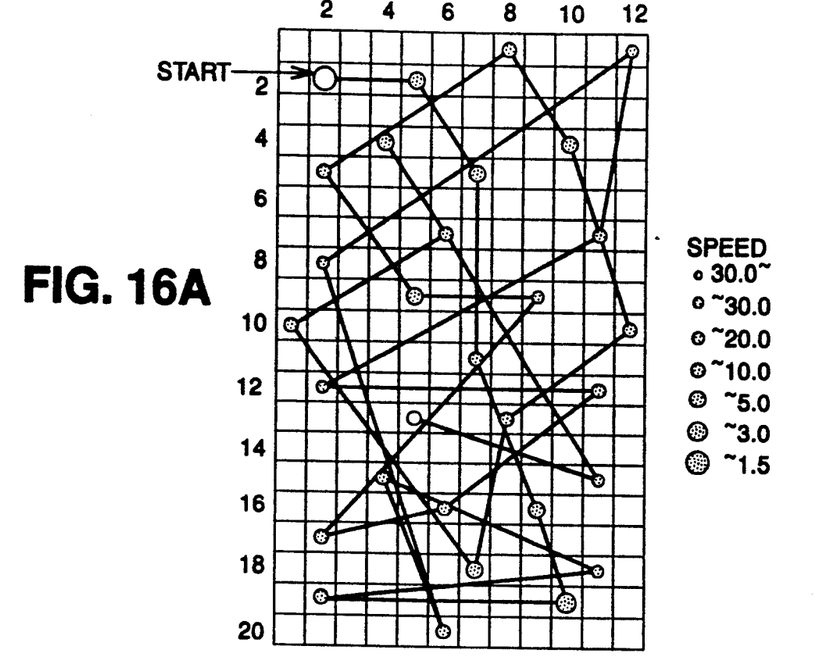
FIGS. 16 and 17 are diagrams showing the speeds developed between points marked by said normal person and patient, respectively.
Figure 16B:
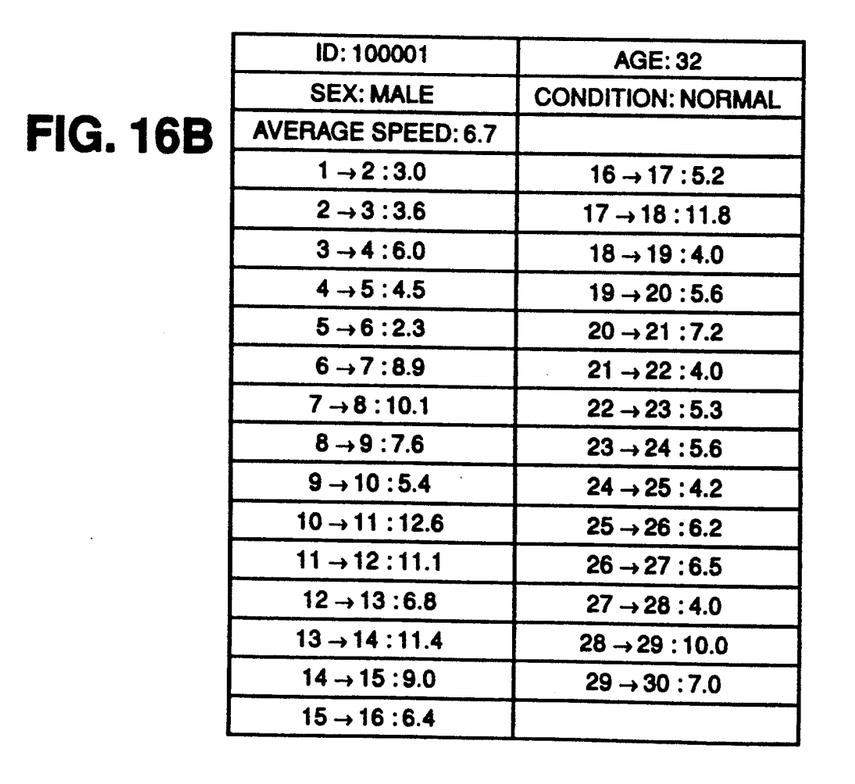
Figure 17A:
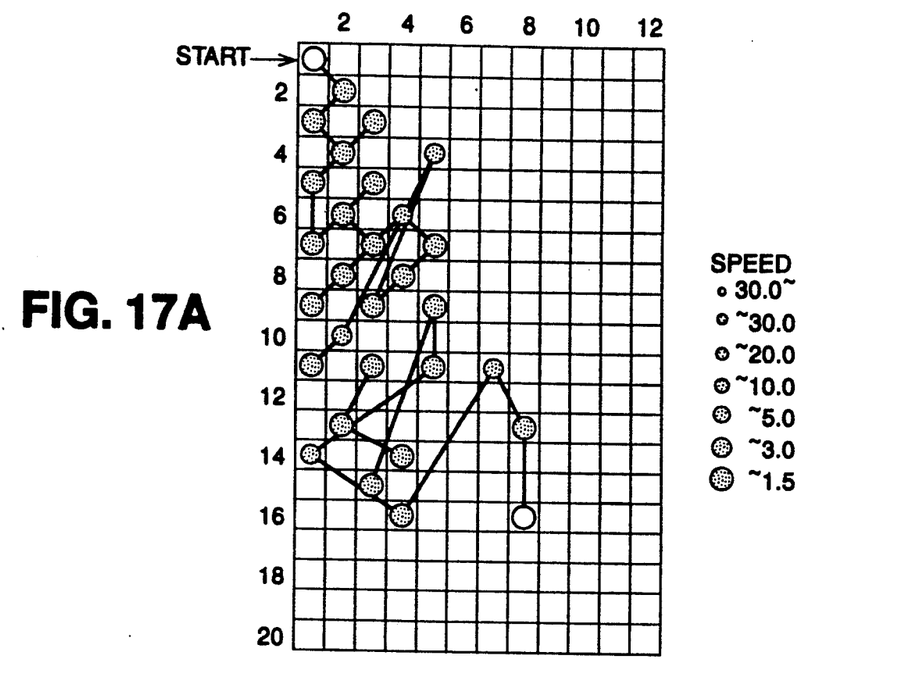
Figure 17B:
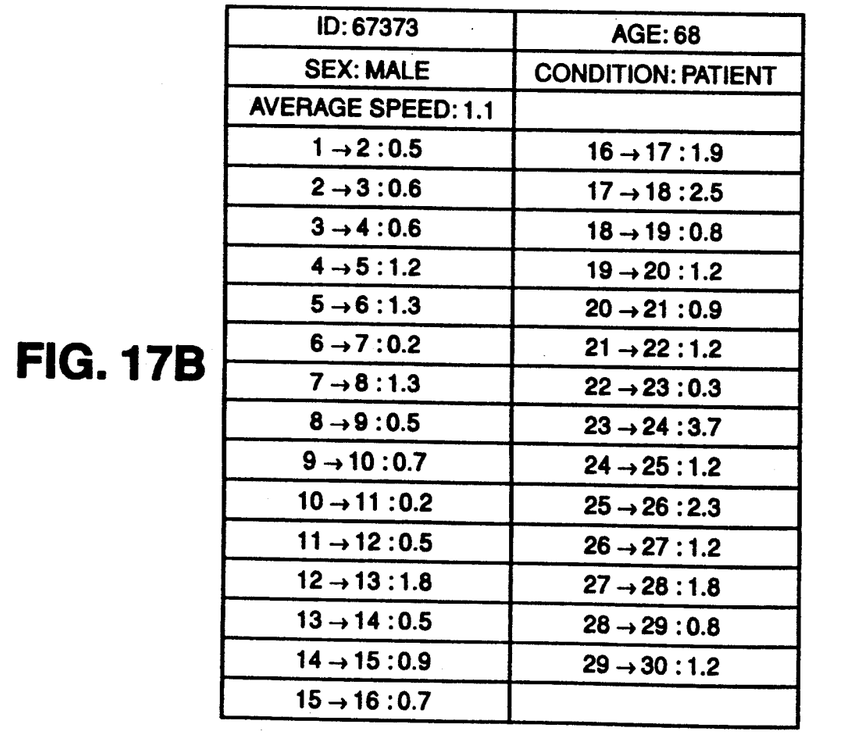

FIGS. 16 and 17 are diagrams showing the speeds developed between points marked by the normal person A and patient B, respectively. The graphs (a) indicate the size of the speed by the size of points, and the successive points are connected by lines so that the order of marking the points can be known. The first and thirtieth points are indicated in different colors on the screen for clarity, and the tables (b) indicate the speed between marked points by numerals.

A comparison between FIGS. 16 and 17 reveals that for the patient, the dispersion is worse, the speed is lower and the amount of movement is smaller.

INDUSTRIAL APPLICABILITY

As has so far been described in detail, according to the present invention, in diagnosing dementia by telling patients to mark points, test results can be quickly obtained, achieving the effect that testing conditions can be simply reproduced.

In the case of other diseases than dementia, such as depression and schizophrenia, there is a possibility that the dispersion of points becomes worse. It seems that the separation of them becomes possible by using a reinstruction method; basically, taking time into consideration offers a greater prospect. That is, possibilities of application to other diseases than dementia are as follows.

Character, habits, conditions and the like of an examinee can be found by the locus produced.
   Finding the degree of stress.
   Whether an examinee is fit for engineering work or clerical work can be found.
   Intelligence test is possible.
   Aptitude test is possible.
   Reflex test is possible.
   Various training checks.

What is claimed is:
1. An intelligence testing device comprising
   a two-dimensional coordinate reader for reading the coordinates of the distribution of points marked by an examinee in a frame defined on a testing block as he is instructed to mark said frame randomly and distributively,
   a storing device for storing the coordinates of said marked points, the order of marking said points or the lapse of time between points,
   a central processing unit for calculating at least (1) the dispersion in the distribution of points, (2) the amount of movement between successively marked points or (3) the dispersion of movement or displacement between successively marked points, and
   a display device for displaying the results of the calculations made by said central processing unit.

2. A device as set forth in claim 1, characterized in that said central processing unit performs said calculations as to the distributions of points marked by a group of examinees regarded as having normal mentation and determines the normal range from the results of calculations, and said display device displays said normal range and the results of calculations concerning the examinees within the same coordinate system.

3. A device as set forth in claim 1, characterized in that in the case where said defined frame comprises a quadrature matrix having M columns and N rows and where said the total number of points which the examinee is instructed to mark is I,
   letting $m_k$ be the number of quadratures marked with points belonging to the k-th column (where k = 1, 2, ..., M) and $n_t$ be the number of quadratures marked with points belonging to the t-th row (where t = 1, 2, ..., N), said calculation (1) calculates $$D_x = \sum_{K=1}^{M} |m_K - I/M|$$

$$D_y = \sum_{t=1}^{N} |n_t - I/N|$$

and specifies the xy coordinates ($T_x$, $T_y$).

4. A device as set forth in claim 1, characterized in that in the case where said defined frame comprises a quadrature matrix having M columns and N rows and where said the total number of points which the examinee is instructed to mark is I,
   letting ui be the distance (the number of quadratures) in the direction of the rows traveled from the i-th point (i = 1, 2, ..., I−1) to the i+1-th point and vi be the distance (the number of quadratures) in the direction of the columns, said calculation (2) finds $$X = \sum_{i=1}^{I-1} |u_i|$$

$$Y = \sum_{i=1}^{I-1} |v_i|$$

and specifies the coordinates (X, Y) and fines the amount of movement S (X, Y) from S (X, Y) = XY.

5. A device as set forth in claim 1, characterized in that in the case where said defined frame comprises a quadrature matrix having M columns and N rows and where said the total number of points which the examinee is instructed to mark is I,
   letting $\nu_k$ be the number of quadratures marked with points belonging to the k-th column (where k = 1, 2, ..., M) and $\lambda_t$ be the number of times of marking of points with a distance traveled by an amount corresponding to k quadratures from the preceding marked point in the direction of the rows, the calculation (3) finds $T_x$ and $T_y$ from $$T_x = \sum_{k=-(M-1)}^{M-1} \left| \nu_k - \frac{M - |k|}{M_2} \times (I - 1) \right|$$

$$T_y = \sum_{t=-(N-1)}^{N-1} \left| \lambda_t - \frac{N - |t|}{N_2} \times (I - 1) \right|$$

and specifies the coordinates ($T_x$, $T_y$).

* * * * *